(12) United States Patent
Liu

(10) Patent No.: US 6,932,960 B2
(45) Date of Patent: Aug. 23, 2005

(54) N-SUBSTITUTED 3-HYDROXY-4-PYRIDINONES AND PHARMACEUTICALS CONTAINING THEREOF

(75) Inventor: Shuang Liu, Chelmsford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/803,724

(22) Filed: Mar. 18, 2004

(65) Prior Publication Data

US 2004/0176326 A1 Sep. 9, 2004

Related U.S. Application Data

(62) Division of application No. 10/358,835, filed on Feb. 5, 2003, now Pat. No. 6,825,204.
(60) Provisional application No. 60/354,339, filed on Feb. 5, 2002.

(51) Int. Cl.$^7$ ............................. A61K 51/00; C07F 5/00
(52) U.S. Cl. ...................... 424/1.65; 534/10; 546/193; 546/296; 544/131
(58) Field of Search ....................... 424/1.65; 534/10; 546/193, 296; 544/131

(56) References Cited

U.S. PATENT DOCUMENTS

| | | | |
|---|---|---|---|
| 2,136,807 A | 11/1938 | Stoker | 110/48 |
| 4,908,371 A | 3/1990 | Moerker et al. | 514/318 |
| 5,087,440 A | 2/1992 | Cacheris et al. | 424/9 |
| 5,155,215 A | 10/1992 | Ranney | 534/16 |
| 5,256,676 A | 10/1993 | Hider et al. | 514/348 |
| 5,525,326 A | 6/1996 | Unger | 424/9.36 |
| 5,527,790 A | 6/1996 | McNeill et al. | 514/186 |
| 5,688,815 A | 11/1997 | Zbinden et al. | 514/348 |
| 5,716,598 A | 2/1998 | Golman et al. | 424/9.36 |
| 5,866,563 A | 2/1999 | McNeil et al. | 514/186 |
| 5,877,210 A | 3/1999 | Schieven | 514/492 |
| 5,980,863 A | 11/1999 | Harnish et al. | 424/9.36 |
| 6,046,219 A | 4/2000 | Hanauske-Abel et al. | 514/348 |
| 6,232,340 B1 | 5/2001 | Zhang et al. | 514/492 |
| 6,294,152 B1 | 9/2001 | Davies et al. | 424/9.361 |
| 6,323,340 B1 | 11/2001 | Masuda et al. | 514/492 |

FOREIGN PATENT DOCUMENTS

| | | |
|---|---|---|
| EP | 0 316 279 A2 | 5/1989 |
| EP | 0 335 745 | 10/1989 |
| EP | 1 006 108 | 6/2000 |
| EP | 1 006 112 | 6/2000 |
| GB | 2 269 589 | 2/1994 |
| GB | 2 345 058 | 6/2000 |
| JP | 07 179 474 | 7/1995 |
| WO | WO 91/12822 | 9/1991 |
| WO | WO 93/10822 | 6/1993 |
| WO | WO 96/05867 | 2/1996 |
| WO | WO 96/22021 | 7/1996 |
| WO | WO 96/41639 | 12/1996 |
| WO | WO 97/02842 | 1/1997 |
| WO | WO 98/01458 | 1/1998 |
| WO | WO 98/54138 | 12/1998 |
| WO | WO 99/23075 | 5/1999 |
| WO | WO 99/30562 | 6/1999 |
| WO | WO 00/16736 | 3/2000 |
| WO | WO 00/16782 | 3/2000 |
| WO | WO 00/24730 | 5/2000 |
| WO | WO 01/12168 | 2/2001 |

OTHER PUBLICATIONS

Abeysinghe, R.D., et al., "The environment of the lipoxygenase iron binding site explored with novel hydroxpyridine iron chelators," *J. of Biological Chem.*, 1996, 271(44), 7965–7972.

Ahmed, S.I., et al., "The structures of bis–maltolato–zinc(II) and of bis–3–hydroxy–1,2–dimethyl–4–pyridinonato–zinc(II) and–lead(II)," *Polyhedron*, 2000, 19, 129–135.

Barret, M.C., et al., "Synthesis and structural characterization of Tin(II) and Zinc(II) derivatives of cyclic α–hydroxyketones, including the structures of Sn(mltol)$_2$, Sn(troplone)$_2$, Zn(troplone)$_2$, and Zn(hinokitiol)$_2$," *Inorg. Chem.*, 2001, 40, 4384–4388.

Bebbington, D., et al., "3,5–disubstituted–4–hydroxyphenyls linked to 3–hydroxy–2–methyl–4–(1H)–pyridione: potent inhibitors of lipid peroxidation and cell toxicity," *J. Med. Chem.*, 2000, 43, 2779–2782.

Bickerdike, M.J., et al., "Enhanced acetylcholine release in striatum after chronic amphetamine is NMDA–dependent," *NeuroReport*, 1999, 10, 77–80.

Bosquet, J.–C., et al., "Gd–DOTA: characterization of a new paramagnetic complex," *Radiology*, 1988, 166, 693–698.

Branen, A. L., et al., "Use of antioxidants in self–preserving cosmetic and drug formulations," *Cosmet. Sci. Technol. Ser.*, 1997, 16, 159–179.

Brewer, G.J., "Cooper control as an antiangiogenic anticancer therapy: lessons from treating Wilson's Disease," *Exp. Biol. Med.*, 2001, 226(7), 665–673.

CAPLUS Accession No. 1995:887972 (English abstract of Japanese Patent).

Caravan, P., et al., "Gadolinium(III) chelates as MRI constrast agents: structure, dynamics and applications,", *Chem. Rev.*, 1999, 99, 2293–2352.

Caravan, P., et al., "Reaction chemistry of BMOV, Bis(maltolato)oxovanadium(IV)—apotent insulin mimetic agent," *J. Am. Chem. Soc.*, 1995, 117, 12750–12770.

(Continued)

*Primary Examiner*—Charanjit S. Aulakh
(74) *Attorney, Agent, or Firm*—Woodcock Washburn LLP

(57) ABSTRACT

N-substituted 3-hydroxy-4-pyridinones and metal chelates, methods of preparing N-substituted 3-hydroxy-4-pyridinones and metal chelates, and pharmaceutical compositions containing new N-substituted 3-hydroxy-4-pyridinones and/or their metal chelates. Use of N-substituted 3-hydroxy-4-pyridinones and their metal chelates as pharmaceutical agents for the treatment of diseases, such as parasitic and viral infections, conditions associated with inflammation and infection, and conditions mediated by cell-proliferation or collagen formation.

6 Claims, No Drawings

OTHER PUBLICATIONS

Clarke, E.T., et al., "Stabilities of 1,2–dimethyl–3–hydroxy–4–pyridinone chelates of divalent and trivalent metal ions," *Inorganica Chimica Acta*, 1992, 191, 57–63.

Dobbin, P.S., et al., "Synthesis, physicochemical properties, and biological evaluation of N–substituted 2–alkyl–3–hydroxy–4(1H)–pyridinones: orally active iron chelators with clinical potential," *J. Med. Chem.*, 1993, 36, 2448–2458.

Dutt, N.K., et al., "Chemistry of lanthanons—XL1. isolation and characterization of tris chelates of lanthanides with maltol, kojic acid and chloro–kojic acid," *J. Inorg. Nucl. Chem.*, 1975, 37, 1801–1802.

Edwards, D.S., et al., "Characterization of Tris(N–substituted–2–methyl–3–hydroxy–4–pyridinonato)technetium(IV)cations," *Inorg. Chem.*, 1994, 33, 5607–5609.

Edwards, D.S., et al., "Potential $^{99m}$Tc radiopharmaceuticals for renal imaging: tris(N–substituted–3–hydroxy–2–methyl–4–pyridinonato)technetium(IV)cations," *Nucl. Med. Biol.*, 1993, 20(7), 857–863.

El–Jammal, A., et al., "Cooper complexation by 3–hydroxypyridin–4–one iron chelators: structural and iron competition studies," *J. Med. Chem.*, 1994, 37, 461–466.

Ellis, B.L., et al., "6–alkoxymethyl–3–hydroxy–4H–pyranones: potential ligands for cell–labeling with indium," *Eur. J. Nucl. Med.*, 1999, 26, 1400–1406.

Ellis, B.L., et al., "Synthesis, physicochemical properties, and biological evaluation of hydroxypyranones and hydroxypyridinones: novel bidentate ligands for cell–labeling," *J. Med. Chem.*, 1996, 39, 3659–3670.

Faller, B., et al., "Improving the oral bioavailability of the iron chelator HBED by breaking the symmetry of the intramolecular H–bond network," *J. Med. Chem.*, 2000, 43, 1467–1475.

Fernandez, J.A., et al., "Essential viral and cellular zinc an iron containing metalloproteins as targets for novel antiviral and anticancer agents: implications for prevention and therapy of viral diseases and cancer," *Anticancer Res.*, 2001, 21, 931–958.

Ferrali, M., et al., "3–hydroxy–(4H–)–benzopyran–4–ones as potential iron chelating agents in vivo," *Bioorganic & Medicinal Chem.*, 2001, 9, 3041–3047.

Foda, H.D., et al., "Matrix metalloproteinases in cancer invasion, metastasis and angiogenesis," *DDT*, 2001, 9, 478–482.

Gutteridge, J.M.C., et al., "Iron toxicity and oxygen radicals," *Ballièr's Clin. Haematology*, 1989, 2(2), 195–256.

Gwyn, K., et al., "Breast cancer during pregnancy," *Oncology*, 2001, 15(1), 39–46.

Hashimoto, M., et al., "Oxidative stress induces amyloidlike aggregate formation of NACP/α–synuclein in vitro," *NeuroReport*, 1999, 10, 717–721.

Henrotin, Y., et al., "The inhibition of metalloproteinases to treat osteoarthritis: reality and new perspectives," *Expert Opin. Ther. Patents*, 2002 12(1), 29–43.

Hidalgo, M., et al., "Development of matrix metalloproteinase inhibitors in cancer therapy," *J. of the National Cancer Institute*, 2001, 93(3), 178–193.

Hider, R.C., et al., "Design of orally active iron chelators," *Acta Haematol*, 1996, 95, 6–12.

Hu, T.C.–C., et al., "Manganese–enhanced MRI of mouse heart during changes in inotropy," *Magnetic Resonance in Medicine*, 2001, 46, 884–890.

Hunter, D.R., et al., "Comparison of $Ca^{2+}$, $SR^{2+}$, and $Mn^{2+}$ fluxes in mitochondria of the perfused rat heart," *Circ. Res.*, 1980, 47, 721–727.

John A., et al., "The role of matrix metalloproteinases in tumor angiogenesis of tumor metastasis," *Pathology Oncology Res.*, 2001, 7(1), 14–23.

Liu, Z.D., et al., "Design, synthesis and evaluation of N–basis substituted 3–hydroxypryridin–4–ones: orally active iron chelators with lysosomotrophic potential," *J. Pharm. Pharmacol.*, 2000, 52, 263–272.

Liu, Z.D., et al., "Structure–activity investigation of the inhibition of 3–hydroxypyridin–4–ones on mammalian tyrosine hydroxylase," *Biochem. Pharmac.*, 2001, 285–290.

Liu, Z.D., et al., "Synthesis of 2–amido–3–hydroxypyridin–4(1H)–ones: novel iron chelators with enhanced pFe$^{3+}$ values," *bioorganic & Medicinal Chem.*, 2001, 9, 563–573.

Magerstädt, M., et al., "Gd(DOTA): an alternative to Gd(DTPA)as a $T_{1,2}$ relaxation agent for NMR imaging or spectroscopy," *Magnetic Resonance in Medicine*, 1986, 3, 808–812.

Martell, A.E., et al., "New chelating agents suitable for the treatment of iron overload," *Inorganica Chimica Acta*, 1999, 291, 238–246.

Matthews, A.J., et al., "Iron and atherosclerosis: inhibition by the iron chelator deferiprone (L1)," *J. of Surg. Res.*, 1997, 73, 35–40.

McCawley, L.J., et al., "Matrix metalloproteinases: multifunctional contributors to tumor progression," *Molecular Medicine Today*, 2000, 6, 149–156.

McNeill, J.H., et al., "Bis(maltolato)oxovanadium(IV) is a potent insulin mimic," *J. Med. Chem.*, 1992, 35, 1489–1491.

Melchoir, M., et al., "Vanadium complexes as insulin mimetic agents: coordination chemistry and in vivo studies of oxovanadium(IV) and dioxovanadate(V) complexes formed from naturally occurring chelating oxazolinate, thiazolinate, or picolinate units," *Inorg. Chem.*, 1999, 38, 2288–2293.

Molenda, J.J., et al., "Enhancement of iron excretion via monoanionic 3–hydroxypyrid–4–ones," *J. Med. Chem.*, 1994, 37, 93–98.

Narita, K., et al., "Mn and Mg influxes through Ca channels of motor nerve terminals are prevented by verapamil in frogs," *Brain Res.*, 1990, 510, 289–295.

Naughton, D.P., et al., "EDTA bis–(ethyl phenylalaninate): a novel transition metal–ion chelating hydroxyl radical scavenger with a potential anti–inflammatory role," *Bioorganic & Medicinal Chem. Letts.*, 2001, 11, 2573–2575.

Piyamongkol, S., et al., "Novel synthetic approach to 2–(1'–hydroxyalkyl)–and 2–amido–3–hydroxypyridin–4–ones," *Tetrahedron*, 2001, 57, 3479–3486.

Porter, J.B., "A risk–benefit assessment of iron–chelation therapy," *Drug Safety*, 1997, 17(6), 407–421.

Rai, B.L., et al., "Synthesis, physicochemical properties and biological evaluation of ester prodrugs of 3–hydroxypyridin–4–ones: design of orally active chelators with clinical potential," *Eur. J. Med. Chem.*, 1999, 34, 475–485.

Rai, B.L., et al., "Synthesis, physiocochemical properties, and evaluation of N–substituted–2–alkyl–3–hydroxy–4–(1H)–pyridinones," *J. Med. Chem.,* 1998, 41, 3347–3359.

Rangel, M., "Pyridinone oxovanadium(IV) complexes: a new class of insulin mimetic compounds," *Transition Metal Chem.,* 2001, 26, 219–223.

Remington's Pharmaceutical Sciences, 17th Ed., *Mack Publishing Co.,* 1985, p. 1418.

Runge, V.M., "Safety ofapproved MR contrast media for intravenous injection," *J. of Magnetic Resonance Imaging,* 2000, 12, 205–213.

Runge, V.M., et al., "MR imaging of rat brain glioma: Gd–DTPA versus Gd–DOTA," *Radiology,* 1988, 166, 835–838.

Sakurai, H., et al., "Cysteine methyl ester–oxovanadium(IV) complex, preparation and characterization," *Inorganica Chimica Acta,* 1980, 46, L119–L120.

Shibuya, I., et al., "Indications from Mn–quenching of fura–2 fluorescence in melanotrophs that dopamine and baclofen close Ca channels that are spontaneously open by not those opened by high $[K^+]_o$, and that Cd preferentially blocks the latter," *Cell Calcium,* 1993, 14, 33–44.

Singh, S., et al., "Urinary metabolic profiles in human and rat of 1,2–dimethyl– and 1,2–diethyl–substituted 3–hydroxypyridin–4–ones," *Drug Metabolism andDisposition,* 1992, 20(2), 256–261.

Skiles, J.W., et al., "The design, structure and therapeutic application of matrix metalloproteinase inhibitors," *Curr. Med. Chem.,* 2001, 8, 425–474.

Streater, M., et al., "Novel 3–hydroxy–2(1H)–pyridinones. Synthesis, iron(III)–chelating properties, and biological activity," *J. Med. Chem.,* 1990, 33, 1749–1755.

Thomas, et al., "Chemotherapeutic studies in the heterocyclic series. Reaction of kojic acid with hydrazine. Reaction of kojic acid ethers with hydrazine," *Helvetica Chimica Acta,* 1960, 43, 469–477.

Thomspon, K.H., et al., "Coordination chemistry of vanadium in metallopharmaceutical candidates compounds," *Coordination Chem. Rev.,* 2001, vol. 219–221, 1033–1053.

Thompson, K.H., et al., "Design of vanadium compounds as insulin enhancing agents," *J. Chem. Soc.,* Dalton Trans., 2000, 2885–2892.

Whittaker, M., et al., "Design and therapeutic application of matrix metalloproteinase inhibitors," *Chem. Rev.,* 1999, 99, 2735–2776.

Yuen, V.G., et al., "Comparison of the glucose–lowering properties of vanadyl sulfate and bis(maltolato)oxovanadium(IV) following acute and chronic administration," *Can. J. of Physiol. Pharmacol.,* 1995, 73, 55–64.

Yuen, V.G., et al., "Glucose–lowering properties of vanadium compounds: comparison of coordination complexes with maltol or Kojic acid as ligands," *J. of Inorganic Biochem.,* 1997, 68, 109–116.

Yuen, V.G., et al., "Effect of low and high dose administration of bis(maltolato)oxovanadium(IV) on *fa/fa* zucker rats," *Can. J. Physiol. Pharmacol.,* 1996, 74, 1001–1009.

Zhang, Z., et al., "Potential $^{67}$Ga radiopharmaceuticals for myocardial imaging: Tris(1–aryl–3–hydroxy–2–methyl–4–pyridinonato)gallium(III) complexes," *Nucl. Med. Boil.,* 1992, 19(3), 327–335.

Dobbin, P.S., et al., "Synthesis, physicochemical properties, and biological evaluation of N–substituted 2–alkyl–3–hydroxy–4(1H)–pyridinones: orally active iron chelators with clinical potential," *J. Med. Chem.,* 1993, 36, 2448–2458.

Edwards, D.S., et al., "Characterization of Tris(N–substituted–2–methyl–3–hydroxy–4–pyridinonato)technetium(IV) cations," *Inorg. Chem.,* 1994, 33, 5607–5609.

Melchior, M., "Vanadium complexes as insulin mimetic agents: coordination chemistry and in vivo studies of oxovanadium(IV) and dioxovanadate(V) complexes formed from naturally occurring chelating oxazolinate, thiazolinate, or picolinate units," *Inorg. Chem.,* 1999, 38, 2288–2293.

Rai, B.L., et al., "Synthesis, physicochemical properties, and evaluation of N–substituted–2–alkyl–3–hydroxy–4(1H)–pyridinones," *J. Med. Chem.,* 1998, 41, 3347–3359.

N-SUBSTITUTED 3-HYDROXY-4-PYRIDINONES AND PHARMACEUTICALS CONTAINING THEREOF

This application is a divisional application of U.S. application Ser. No. 10/358,835 filed Feb. 5, 2003 now U.S. Pat. No. 6,825,204 now allowed, which claims the benefit of priority of U.S. Provisional Application No. 60/354,339 filed Feb. 5, 2002, both of which are hereby incorporated by reference.

FIELD OF THE INVENTION

This invention relates to novel N-substituted 3-hydroxy-4-pyridinones and metal chelates, methods of preparing N-substituted 3-hydroxy-4-pyridinones and metal chelates, and pharmaceutical compositions containing new N-substituted 3-hydroxy-4-pyridinones and/or their metal chelates. This invention also relates to the use of N-substituted 3-hydroxy-4-pyridinones and their metal chelates as pharmaceutical agents for the treatment of diseases, such as parasitic and viral infections, conditions associated with inflammation and infection, and conditions mediated by cell-proliferation or collagen formation. This invention particularly relates to the N-substituted 3-hydroxy-4-pyridinones as chelators for chelation therapy of iron overload. This invention also relates to the use metal chelates of N-substituted 3-hydroxy-4-pyridinones as NMR contrast agents or radiopharmaceuticals.

BACKGROUND OF THE INVENTION

There are a number of inherited diseases, which are associated with the gradual accumulation of iron. These include β-thalassaemia major and thalassaemia intermedia. Due to its facile redox chemistry, excess iron in human body often results in irreversible damage to endocrine organs and lethal cardiac toxicity. In humans such excess iron can not be excreted via normal routes, namely, the urine and the bile, and consequently chelation therapy is essential (*J. Med. Chem.* 1998, 41: 3347–3359; *Inorg. Chem. Acta* 1999, 291: 238–246).

The objectives of iron-chelation therapy for iron overload are two fold: first, to produce negative iron balance by removing excess body iron; and second, to detoxify the excess iron while, and until, the first objective is achieved (*Drug Safety* 1997, 17: 407–421). In order to be considered harmless, iron must be fully coordinated. If any of its six coordination sites remain uncoordinated, iron will participate in Fenton reactions, resulting in lipid peroxidation with organelle and cell damage from hydroxyl radicals (*Baillieres Clin. Haematol.* 1989, 2: 195–256). Therefore, the iron chelator has to be able to form the iron complex with extremely high stability. Specificity of iron binding over other metals (e.g., zinc and copper) is also necessary to avoid chelation of these metals, which are needed for normal physiological activities.

Ideally, an iron chelator should have a low degree of penetration into the central nerve system and should produce a high degree of extraction of iron from hepatic cells, where iron is present in high levels (*Drug Safety* 1997, 17: 407–421; *Acta Haematol.* 1996, 95: 6–12). A second constraint of chelator design is that iron must not be redistributed from liver to other parts (e.g., heart and joint) of the body where it may be harmful. This requires that the iron complex be extremely stable. For a chelator to be efficiently absorbed from the gut, the molecular weight of the chelator has to be about 400 Dalton.

There has been considerable interest in the design of orally active iron chelators over the last two decades and many high-affinity iron chelators have been prepared (*J. Med. Chem.* 1990, 33: 1749–1755; *J. Med. Chem.* 1993, 36: 2448–2458; *J. Med. Chem.* 1993, 36: 2448–2458; *J. Med. Chem.* 1994, 37: 461–466; *J. Med. Chem.* 1994, 37: 93–98; *J. Med. Chem.* 1998, 41: 3347–3359; *Eur. J. Med. Chem.* 1999, 34: 475–485; *J. Med. Chem.* 2000, 43: 1467–1475, *J. Pharm. Pharmacol.* 2000, 52: 263–272; *Bioorg. Med. Chem.* 2001, 9: 563–573; *Bioorg. Med. Chem.* 2001, 9: 3041–3047; *Tetrahedron* 2001, 57:3479–3486). As a result, 1,2-dimethyl-3-hydroxypyridin-4-one (DMHP, CP20, Deferiprone) has been selected as the clinical candidate for the treatment of iron overload. One of the problems with such an N-alkyl-3-hydroxypyridin-4-one is the ability of the free ligand and the resulting iron complex to rapidly penetrate cell membranes and other biological barriers (*Drug Met. Disp.* 1992, 20: 256–261). A second problem is that N-alkyl-3-hydroxypyridin-4-ones are rapidly metabolized by glyceronidation of the 3-hydroxy group, which will lead to disappearance of iron-chelating properties of the molecule. Despite recent developments, there is a continuing need for new iron chelators, which have high binding affinity for iron and are able to accumulate in liver, the major storage organ in iron-overload conditions.

For many years radical scavenging antioxidants have been successfully used to protect synthetic material and food products from degradating process of oxidation (*Cosmet. Sci. Technol. Ser.* 1997, 16: 159–179). Radical scavengers have been proposed as neuroprotective agents for the treatment of disorders known to involve oxidative stress, such as stroke, tramatic brain injury, spinal cord injury, cerebral tumor, subharrchnoid haemorrage/cerebral vasospam, cerebral ischaemia, stroke, Alzheimers' disease, Huntington's disease, Parkinson's disease, Friedrich ataxia, motor neuron disease or multiple sclerosis. However, the effectiveness of radical scavengers in reducing oxidative stress within living biological environment is often undermined by the continual production of free radicals mediated by iron. Since Fe is involved in the production of toxic free radicals, several radical scavenger-conjugated 3-hydroxy-4-pyridinones have been prepared and studied as potent inhibitors of lipid peroxidation and cell toxicity (*J. Med. Chem.* 2000, 43: 2779–2782). Some display a superior neuroprotective activity compared to dual administration of the radical scavenger, di-tert-butylphenol, and the iron chelator, Deferiprone, demonstrating the synergistic effect between the radical scavenger and the iron chelator.

Vanadium compounds, in vitro, stimulate glucose uptake and inhibit lipid break down, in a manner remarkably reminiscent of insulin's effect. Vanadium chelates with organic chelators present ways to fine tune the effect of vanadium, thereby minimizing any adverse effects without sacrificing important therapeutic benefits. Many compounds have been proposed as "insulin mimetics". These include vanadium complexes of pyronates (*J. Med. Chem.* 1992, 35: 1489–1491; *J. Am. Chem. Soc.* 1995, 117: 12759–12770; *Can. J. Physiol. Pharmacol.* 1995, 73: 55–64; *Can. J. Physiol. Pharmacol.* 1996, 74: 1001–1009; *J. Inorg. Biochem.* 1997, 68: 109–116;), pyridinates (*Transition Metal Chem.* 2001, 26: 219–223), picolinates (*Inorg. Chem.* 1999, 38: 2288–2297), and cycteine ester (*Inorg. Chim. Acta* 1980, 46: 2288-L119–L125), and have been recently reviewed (*J. Chem. Soc., Dalton Trans.* 2000, 2885–2892; *Coord. Chem. Rev.* 2001, 219–221: 1033–1053).

For vanadium to be useful as an orally available insulin mimetic agent, it must be able to cross biological membranes, both for the initial absorption process and intracellular uptake. Therefore, the metal chelate must have low molecular weight, neutral charge, and a fair degree of resistance to hydrolysis. The lipophilicity of the metal chelates must be balanced with its hydrophilicity, and possess adequate thermodynamic stability. As bidentate chelators for the design of vanadium chelates useful as insulin enhancing agents, 3-hydroxy-4-pyrones and 3-hydroxy-4-pyridinones are exemplary. Both 3-hydroxy-4-pyrones and 3-hydroxy-4-pyridinones form stable and neutrally charged vanadium chelates, which have an optimal combination of water solubility, reasonable hydrolytic stability, and significant lipophilicity (*J. Chem. Soc., Dalton Trans.* 2000, 2885–2892; *Coord. Chem. Rev.* 2001, 219–221: 1033–1053).

N-Alkyl-3-hydroxy-4-pyridinones form very stable six-coordinated gadolinium chelates (*Inorg. Chim. Acta* 1992, 191: 57–63), potentially useful as MRI contrast agents. They also form very stable Zn(II) and Tin(II) complexes, which are useful in dental care formulations (*Polyhedron* 2000, 19, 129–135; *Inorg. Chem.* 2001, 40, 4384–4388). In addition, $^{67}$Ga, $^{111}$In and $^{99m}$Tc complexes of N-alkyl-3-hydroxy-4-pyridinones have been studied as potential radiopharmaceuticals either for imaging or for the radiolabeling of white blood cells (*Nucl. Med. Biol.* 1992, 19: 327–335; *Nucl. Med. Biol.* 1993, 20, 857–863; *Inorg. Chem.* 1994, 33, 5607–5679; *J. Med. Chem.* 1996, 39: 3659–3670; *Eur. J. Nucl. Med.* 1999, 26: 1400–1406). Other potential applications for substituted 3-hydroxy-4-pyridinones also include their use for the treatment of overload of other metals (e.g., copper, zinc, aluminum and plutonium) present in the body in deleterious amounts, inflammatory disease (*J. Biol. Chem.* 1996, 271: 7965–7972; *Bioorg. Med. Chem. Lett.* 2001, 11: 2573–2575), atherosclerotic disease (*Neuroreport* 1999, 10: 717–725), neoplastic disease, and thrombosis.

UK Patent No. 2 136 807 discloses the use of 3-hydroxy-4-pyridinones for the treatment of iron overload arising from various causes, particularly that arising from pathological conditions such as thalassaemia, sickle cell anaemia, asplatic anaemia, and idiopathic haemochromatosis, often through the treatment of the first three conditions by regular blood transfusions. In addition, 3-hydroxy-4-pyridinones are of interest for the treatment of pathological conditions where there may be an excess of iron deposited at certain sites even though patients do not exhibit a general iron overload.

EP Patent No. EP0335745 A1 discloses a process for preparation of substituted 3-hydroxy-4-pyridinones. EP Patent No. EP0768302A2 and UK Patent No. GB2 269 589A also disclose synthesis of N-substituted 3-hydroxy-4-pyridinones and pharmaceutical compositions containing thereof. The substituent at the N atom is an aliphatic hydrocarbon group.

U.S. Pat. No. 5,256,676 discloses synthesis of N-substituted 3-hydroxy-4-pyridinones and a method for the treatment of a patient having a condition caused by an iron-dependent parasite which comprises administering to that patient a therapeutically effective amount of N-substituted 3-hydroxy-4-pyridinones.

Proposals have been made in EP Patent No. EP 0316279A2 to modify the 3-hydroxy group of the 3-hydroxy-4-pyridinones to provide a pro-drug form, i.e., in the form of a drug which does not itself possess the desired biological activity but which is converted in vivo to a drug which does. UK Patent No. 2 269 589 specifically discloses the use of substituted 3-hydroxy-4-pyridinones as chelating agents for the treatment of iron overload.

International Publication No. WO 98/54138 discloses preparation of 3-hydroxy-4-pyridinones as orally active iron chelators and their pharmaceutical formulations. The substituent at the N atom contains an aliphatic hydrocarbon group substituted by a hydroxy group or a carboxylic acid ester, sulfonic acid ester or a C1–6-alkoxy or C7–10-aralkoxy ether. International Publication No. WO 98/01458 also discloses preparation of N-substituted 3-hydroxy-4-pyridinones as iron(III) chelators. The N-substituents are selected from polyhydroxycarbons, such as saccharides.

UK Patent No. GB2345058A, International Publication No. WO 99/23075 and European patent applications EP1006108A1 and EP1006112A1 disclose preparation of N-substituted hydroxypyridinone derivatives as reactive oxygen species scavengers. The N-substituted hydroxypyridinone derivatives contain both ortho-hydroxypyridinone and oxygenated aryl (including heteroaryl) functionalities, which possess the dual ability to chelate iron and scavenge reactive oxygen species. The N-substituted 3-hydroxy-4-pyridinone derivatives are particularly useful for the treatment of a condition associated with oxidative stress, such as oxidative damage of the central nervous system or an acute or chronic neurological disorder such as tramatic brain injury, spinal cord injury, cerebral tumor, subharrchnoid haemorrage/cerebral vasospam, cerebral ischaemia, stroke (ischaemic or haemorragic), Alzheimers' disease, Huntington's disease, Parkinson's disease, Friedrich ataxia, motor neuron disease or multiple sclerosis.

U.S. Pat. No. 6,046,219 and International Publication Nos. WO 96/22021, WO96/41639, and WO 99/30562 disclose the use of hydroxypyridinone derivatives useful for the treatment of fibroproliferative disorders by inhibiting protein hydroxylation. Inhibitors of protein hydroxylases (including aspartyl/asparaginyl hydroxylase, prolyl 4-hydroxylase, and deoxyhypusine hydroxylase) block the biochemical events that are required for the formation of excessive fibrocellular scar tissue, and therefore have anti-fibroproliferative properties of clinic importance.

U.S. Pat. No. 5,877,210 discloses a conjugate comprising an inhibitor of phosphotyrosine phosphatase covalently conjugated to a specific binding partner for a cell surface receptor found on B cells, wherein the inhibitor of phosphotyrosine phosphatase is a compound comprising a metal chelate of an organic chelator selected from the group consist of (a) keto-enol tautomers with the keto and enol groups on adjacent carbon atoms that form 5-membered chelate ring or (b) beta-diketones in which the two keto groups are separated by one carbon atom, that form a 6-membered chelate ring. The metal chelates disclosed include V(IV), Cu(II) and Ga(III) complexes of hydroxypyridinones, hydroxymates and acetylacetone. The inhibitory activity of 3-hydroxy-4-pyridinones on mammalian tyrosine hydroxylase has also been reported recently (*Biochem. Pharmacol.* 2001, 61: 285–290).

International Publication No. WO 01/12168 discloses a pharmaceutical composition comprising an iron chelator and another virus-inhibiting compound for the treatment of viral infection, in particular of the human immunodeficiency (HIV). The iron chelator is selected from the group of hydroxamates or hydroxypyridinones while the viral-inhibiting compound is selected from protease inhibitors or reverse transcriptase inhibitors.

U.S. Pat. No. 6,294,152 discloses Fe(III) complexes of 3-hydroxy-4-pyridinones useful as MRI contrast agents. In all the cases, the N-substituent is a simple or substituted alkyl or aryl group.

International Publication No. WO 91/12822 discloses preparation of Fe(III) and Mn(II) complexes of 3-hydroxy-4-pyridinones useful as MRI contrast agents. The substituents on the pyridinone ring are simple alkyl groups substituted with phosphonate or sulfonate groups.

U.S. Pat. Nos. 5,527,790 and 5,866,563 disclose vanadium compositions for the treatment of elevated blood sugar. Vanadium chelates disclosed include those containing hydroxamates, o-heterocycle-substituted phenolates, 3-hydroxy-4-pyrones, and N-substituted 3-hydroxy-4-pyridinates. In all the cases, the N-substituent is a simple or substituted alkyl or aryl group.

U.S. Pat. No. 6,232,340 discloses organovanadium complexes and pharmaceutical compositions containing hydroxyoxovanadium(V), $\mu$-oxo dimeric vanadium(V), and cis-dioxovanadium(V) complexes for the treatment of diseases or disease states, including use as antiproliferative and/or antimetastatic agents.

International Publication No. WO 93/10822 discloses cationic $^{99m}$Tc(IV) complexes with N-substituted 3-hydroxy-4-pyridinones as diagnostic scintigraphic imaging agents. The N-atom is directly attached to a carbon atom from a simple or substituted alkyl or aryl group.

International Publication No. WO 00/16736 discloses an oral care composition containing antiplaque agents. The antiplaque agents are metal complexes of Cu(II), Zn(II), Sn(II), Fe(II), or Fe(III) with a specific class of cyclic $\alpha$-hydroxylketones, including 3-hydroxy-4-pyrones.

However, there remains a need for therapeutic agents with enhanced efficacy, solution stability, and optimal combination of lipophilicity and hydrophilicity. This invention is directed towards meeting this need.

SUMMARY OF THE INVENTION

One aspect of this invention is to provide novel N-substituted 3-hydroxy-4-pyridinones and pharmaceutical compositions containing these new N-substituted 3-hydroxy-4-pyridinones useful for the treatment of overload of iron and other metals (for example copper, zinc, aluminum and plutonium) present in the body in deleterious amounts.

Another aspect of this invention is to provide a method for the preparation of new N-substituted 3-hydroxy-4-pyridinones.

Another aspect of invention is related to the use of pharmaceutical compositions containing new N-substituted 3-hydroxy-4-pyridinones for the treatment of diseases, such as parasitic and viral infections, conditions associated with inflammation and infection, and conditions mediated by collagen formation.

Another aspect of invention is related to metal chelates of N-substituted 3-hydroxy-4-pyridinones, methods of preparing metal chelates of new N-substituted 3-hydroxy-4-pyridinones.

Another aspect of invention is to provide pharmaceutical agents or compositions containing metal chelates of new N-substituted 3-hydroxy-4-pyridinones for the treatment of diseases, such as viral infections, conditions associated with inflammation and infection, and conditions mediated by cell-proliferation or collagen formation.

Another aspect of invention is related to the use of metal chelates of new N-substituted 3-hydroxy-4-pyridinones as NMR contrast agents.

Another aspect of this invention is related to the use metal chelates of new N-substituted 3-hydroxy-4-pyridinones as diagnostic or therapeutic radiopharmaceuticals.

DETAILED DESCRIPTION OF THE INVENTION

For the last two decades, a large number of N-substituted 3-hydroxy-4-pyridinones have been synthesized and studied as iron chelators for the treatment of iron overload (*J. Med. Chem.* 1998, 41: 3347–3359; *Inorg. Chem. Acta* 1999, 291: 238–246; *Drug Safety* 1997, 17: 407–421; *J. Med. Chem.* 1990, 33: 1749–1755; *J. Med. Chem.* 1993, 36: 2448–2458; *J. Med. Chem.* 1993, 36: 2448–2458; *J. Med. Chem.* 1994, 37: 461–466; *J. Med. Chem.* 1994, 37: 93–98; *J. Med. Chem.* 1998, 41: 3347–3359; *Eur. J. Med. Chem.* 1999, 34: 475–485; *J. Med. Chem.* 2000, 43: 1467–1475, *J. Pharm. Pharmacol.* 2000, 52: 263–272; *Bioorg. Med. Chem.* 2001, 9: 563–573; *Bioorg. Med. Chem.* 2001, 9: 3041–3047; *Tetrahedron* 2001, 57:3479–3486). The N-substituted 3-hydroxy-4-pyridinones of this invention are unique in such a way that the N-atom of the pyridinone ring is directly connected to the N-atom of a dialkylamino or acylamido-N or sulfonylamido-N group rather than a simple or substituted alkyl group. As a result, the dialkylamino, acylamido-N and sulfonylamido-N group imparts increased hydrophilicity. Since the molecular weight of these new chelators is generally <400 Dalton, they are expected to be efficiently absorbed from the gut. The lipophilicity arising from aromatic substituents of the dialkylamino or acylamido-N or sulfonylamido-N group should result in accumulation of the new chelator in hepatic cells, where iron is present in high levels. Like other 3-hydroxy-4-pyridinones previously disclosed, the new chelators form iron complexes with high stability. Therefore, the new N-substituted 3-hydroxy-4-pyridinones of the invention have the potential to be used as pharmaceutical agents for the treatment of overload of iron and other metals (e.g., copper, zinc, aluminum and plutonium) present in the body in deleterious amounts.

The N-substituted 3-hydroxy-4-pyridinones of this invention also have the potential to be used in combination with other pharmaceutical agents for the treatment of diseases. For example, it is known that iron chelation can influence HIV replication by inhibiting DNA synthesis via inactivation of iron-dependent ribonucleotide reductase. It has been demonstrated that the combination use of a virus-inhibiting agent (such as a protease inhibitor or a reverse transcriptase inhibitor) with an iron chelator results in synergistic effect for the treatment of viral infection, in particular of the HIV, (International Publication No. WO 01/12168).

Alternatively, the N-substituted 3-hydroxy-4-pyridinones of this invention can be conjugated to a protease inhibitor or a reverse transcriptase inhibitor via a direct covalent bond or through a metabolically cleaveable linker. In this way, the bioconjugate is bifunctional: inactivation of iron-dependent ribonucleotide reductase and inhibition of protease or reverse transcriptase, resulting in synergistic effect for the treatment of viral infection.

The transition metal ion-dependent formation of hydroxyl radical from hydrogen peroxide in the presence of a reducing agent such as superoxide or ascorbate at low concentration is an important mechanism of "oxidative stress" leading to irreversible cell and tissue damage (*Bioorg. Med. Chem. Lett.* 2001, 11: 2573–2575). Metal-ion mediated oxidative stress has been attributed a role in inflammation, atherosclerosis and Alzheimer's disease. It has been reported that iron chelators function as antioxidants to decrease plaque and aggregate formation in neurodegenerative diseases and atherosclerosis (*J. Surg. Res.* 1997, 73: 35–42; *Neuroreport* 1999, 10: 77–85). Iron chelators with the radical scavenging capability are of great potential for the treatment of disorders known to involve oxidative stress, such as stroke, traumatic brain injury, spinal cord injury, cerebral tumor, subharrchnoid haemorrage/cerebral vasospam, cerebral ischaemia, stroke, Alzheimers' disease, Huntington's disease, Parkinson's disease, or multiple sclerosis.

The N-arylsulfonylamido- and N-arylcarboxylamido-substituted 3-hydroxy-4-pyridinones of this invention are bifunctional with the 3-hydroxy-4-pyridinone moiety for iron chelation to inhibit Fe-mediated free radical formation and the aryl group (such as benzene, pyridine and thiophene) for radical scavenging by reacting with hydroxyl radicals. Aromatic compounds such as phenylalanine and phenols react rapidly with hydroxyl radicals (*Bioorg. Med. Chem. Lett.* 2001, 11: 2573–2575). A synergistic neuroprotective activity has been reported for radical scavenger-conjugated 3-hydroxy-4-pyridinones (*J. Med. Chem.* 2000, 43: 2779–2782).

Zinc- and iron-containing metalloproteins have been studied as possible targets for antiviral and anticancer therapy (*Anticancer Res.* 2001, 21, 931–958; *Exp. Biol. Med.* 2001, 226, 665–673). Viral and cellular zinc finger proteins and iron containing proteins are involved in cell proliferation, neovascularization, apoptosis, and viral infection. Matrix metalloproteinases are zinc metalloenzymes involved in remodeling of extracellular matrix, and play an important role in cancer as well as in numerous other disease (*Drug Discovery Today* 2001, 6: 478–482; *Pathol. Oncol. Res.* 2001, 7: 14–23; *Molecular Medicine Today* 2000, 6: 149–156). It has been proposed that disruption of metalloproteins by iron and zinc chelators is a key factor in controlling viral and proliferative diseases (*Anticancer Res.* 2001, 21, 931–958).

Various hydroxamates have been synthesized and studied as metalloproteinase inhibitors (MMPIs) for the treatment of cancer and other diseases (*Chem. Rev.* 1999, 99: 2735–2776; *Oncology* 2001, 15 (7, suppl.): 39–46; *J. National Can. Res.* 2001, 93: 178–193; *Current Med. Chem.* 2001, 8: 425–474; *Expert Opin. Ther. Patents* 2002, 12: 29–43). A recent U.S. patent (U.S. Pat. No. 6,232,340) discloses vanadium(V) complexes of 3-hydroxy-4-pyrones and N-alkyl 3-hydroxy-4-pyridinones as anti-proliferative and antimetastatic agents. It is not clear if the anti-proliferative and antimetastatic activity is due to the vanadium(V) complexes or from the dissociated chelator (3-hydroxy-4-pyrones or 3-hydroxy-4-pyridinones). However, it is known that Deferiprone (1,2-dimethyl-3-hydroxy-4-pyridinone) binds Zn(II) with high affinity with Log $K_{ZnL/[Zn][L]}$=7.19 (*Inorg. Chem. Acta* 1992, 191, 57–63), and form very stable bis-ligand Zn(II) complexes (*Polyhedron* 2000, 19, 129–135; *Inorg. Chem.* 2001, 40, 4384–4388). The Log $K_{ZnL/[Zn][L]}$ is about 100-fold higher than that of N-hydroxyacetamide (Log $K_{ZnL/[Zn][L]}$ <5), the second smallest hydroxamate. Due to the similarity of 3-hydroxy-4-pyrones and 3-hydroxy-4-pyridinones to hydroxamates, one can envisage that the anti-proliferative and antimetastatic activity of the reported vanadium(V) complexes is actually due to MMP inhibition by the dissociated 3-hydroxy-4-pyrones and 3-hydroxy-4-pyridinones. In this connection, the N-substituted 3-hydroxy-4-pyridinones of this invention have the potential as MMP inhibitors useful for the treatment of cancer and many other diseases.

Bidentate N-substituted 3-hydroxy-4-pyridinones of this invention have low molecular weight (<400 Dalton), and are expected to form neutral vanadium chelate with a fair degree of resistance to hydrolysis. The lipophilicity of the vanadium chelates can be tuned by varying substituents on both the pyridinone ring and arylsulfonylamido or arylcarboxylamido group. Like vandium complexes previously described (*J. Chem. Soc., Dalton Trans.* 2000, 2885–2892; *Coord. Chem. Rev.* 2001, 219–221: 1033–1053), the vanadium complexes of new N-substituted 3-hydroxy-4-pyridinones of this invention have the potential to be used as insulin enhancing agents.

Nuclear magnetic resonance (NMR) is based on the absorption of radio-frequency energy by the magnetic moment of atomic nuclei in samples placed in a strong magnetic field. Magnetic resonance imaging (MRI) of the human body relies mainly on the detection of most abundant type of nuclei, the hydrogen in water (and to some extent, fat). For discrimination of healthy and diseased tissues, adequate contrast is essential. Such contrast depends not only on differences in water concentration, but also on the NMR relaxation times $T_1$ and $T_2$, which in turn are related to local mobility and interactions. MRI has become a widely accepted imaging modality for a variety of diseases. The availability of MRI devices has led to the use of MRI for the diagnosis of disease states and other internal abnormalities. Compared to other imaging modalities, MRI provides superior spatial resolution in tissues, and is safe due to the absence of exposure to X-rays or gamma radiation.

The continued use and rapid development of MRI has stimulated interest in the development of MRI contrast agents. MRI contrast agents increase both $1/T_1$ and $1/T_2$ to varying degrees depending on their nature as well as the applied magnetic field, and are used to improve diagnosis of disease by changing tissue signal intensity. Most MRI contrast agents commercially available or under clinical investigations are metal chelates containing paramagnetic metal ions, such as $Fe^{3+}$, $Gd^{3+}$, and $Mn^{2+}$. Agents such as gadolinium chelates are best visualized using $T_1$-weighted images since the percentage change in $1/T_1$ in tissue is much greater than that in $1/T_2$ (Caravan, P. et al. *Chem. Rev.* 1999, 99, 2293–2352). Iron-oxide particles generally lead to a much larger increase in $1/T_2$ than in $1/T_1$ and are best seen with in $T_2$-weighted scans. The metal chelates have proved to be exceptionally well-tolerated class of contrast media. In particular, gadolinium MRI contrast agents do not show any nephrotoxicity in contrast to iodinated contrast media for CT (Runge, V. M. *J. Magn. Reson. Imaging* 2000, 12, 205–213).

There are three basic interactions between the metal ion and water molecules (U.S. Pat. No. 6,294,152). In an inner-sphere interaction, water molecules bind to and exchange with the metal ion, for a very effective contact. In an outer-sphere interaction, all the coordination sites of the metal ion are occupied by chelator(s) so that the water molecules are affected only through translational diffusion past the paramagnetic metal center. In the second-sphere interaction, the metal ion is wrapped with a set of donor atoms of a chelator or chelators, which form strong hydrogen binding with surrounding water molecules.

$Mn^{2+}$ ion, which may conveniently be used in the form of its salt or chelates, has been proposed as an MRI contrast agent due to the five unpaired electrons in its d-orbitals. Manganese chelates, such as Mn(DPDP) (Teslascan™, Nycomed Amersham PL), Mn(DTPA), Mn(EDTA), Mn(TPPS$_4$) and their derivatives, have been used as MRI contrast agents for detection of liver diseases, cancer, and cardiovascular diseases. Paramagnetic metal chelates are safe as MRI contrast agents due to limited presence of free metal ion in the blood stream. Unfortunately, metal chelates also demonstrate reduced solution relativity relative to free metal ions due to replacement of coordinated water molecules by a chelator. Unlike the free metal ion, these manganese chelates are not known to bind endogenous macromolecules such as albumin. As a consequence, the dosage for metal chelates is much higher than that for the free $Mn^{2+}$ ion.

Manganese(II) chloride has been proposed as an MRI contrast agent using intravenous injection. Indeed, even at very low i.v. dosages (5–10 µM/kg) manganese has been found to be particularly effective as a contrast agent for imaging liver. However, manganese salts, when administered intravenously as a contrast agent, may be teratogenic at clinical doses, and are known to interfere with the normal functioning of the heart by replacing calcium in the calcium pump of the heart.

In order to reduce the direct effect on the heart, oral administration of maganese(II) chloride as a liver imaging agent has been proposed (U.S. Pat. Nos. 5,525,326 and 5,716,598). This ensures the passage of the contrast agent through the liver before entering heart. Although orally administered maganese(II) chloride is not teratogenic, the absorption of maganese(II) chloride through the gut is poor. As a result, the dosage required for clinical efficacy is of the order of 200 µM/kg. Such a high dosage will result in adverse cardiac effects.

International Publication Nos. WO 96/05867 and WO 97/02842, and U.S. Pat. Nos. 5,525,326 and 5,716,598 disclose an contrast media comprising a physiologically tolerable manganese compound, an uptake promoter and a physiologically tolerable carrier or exipient, having a manganese concentration of at least 0.3 mM or being in a dosage unit form containing at least 0.3 mM manganese. The uptake promoter is capable of enhancing manganese transport across the membranes of the gastrointestinal (GI) tract. Compounds which have been found to be suitable for use as uptake promoters include reducing compounds containing an α-hydroxy ketone (—C(OH)—CO—) group, acids containing α- and/or β-hydroxy or amino groups, as well as vitamin D. The preferred α-hydroxy ketones include ascorbic acid, kojic acid, gluconic acid and salicylic acid. The uptake promoters most likely act as weak chelators for $Mn^{2+}$ to form a spectrum of $Mn^{2+}$ containing species, which have better GI uptake when administered orally. The disclosed contrast media are particularly suitable for imaging of the liver.

$Mn^{2+}$ has an ionic radius similar to that of $Ca^{2+}$, and is handled similarly in many biological systems (*Circ. Res.* 1980, 47: 721–727). For example, $Mn^{2+}$ is known to enter cardiac myocytes through voltage-gated calcium channels (*Brain Res.* 1990, 510: 289–295; (*Cell Calcium* 1993, 14: 33–44). Therefore, it has been proposed to use $Mn^{2+}$-containing contrast media to image heart (*Magnetic Resonance in Medicine* 2001, 46: 884–890; International Publication No. WO 96/05867, U.S. Pat. Nos. 5,525,326 and 5,716,598). However, the use of a high dosage of $Mn^{2+}$ often results in cardiac toxicity due to replacement of calcium by manganese. To avoid the problem, $Mn^{2+}$-containing contrast media comprising a mixture of $Mn^{2+}/Ca^{2+}$ salts have been proposed (U.S. Pat. No. 5,980,863). The disclosed counter anions include acetate, gluconate, gluceptate, or lactate. Ascorbic acid has been used as antioxidant to stabilize $Mn^{2+}$ in biological systems.

$Fe^{3+}$ also has five unpaired electrons in its d-orbitals. $Fe^{3+}$ metal ions, which interact with water molecules by inner-sphere mechanism, are very effective for the enhancement of relaxation rate; but high dosage of the free metal ion often causes toxicity due to iron overload. The use of iron chelates reduces the toxicity; but the outer-sphere interaction is less effective in providing relaxation rate enhancement. International Publication No. WO 91/12822 discloses preparation of Fe 3+ and $Mn^{2+}$ complexes of 3-hydroxy-4-pyridinones useful as MRI contrast agents. U.S. Pat. No. 6,294,152 discloses $Fe^{3+}$ complexes of 3-hydroxy-4-pyridinones useful as MRI contrast agents. In all the cases, substituents on the pyridinone ring contain various hydrogen-binding functionalities, which are required for effective second-sphere interactions with surrounding water molecules, thereby enhancement of relaxation rate.

Synthesis of lanthanide complexes of 3-hydroxy-4-pyrones, including maltol and kojic acid, was previously reported (*J. Inorg. Nucl. Chem.* 1975, 37: 1801–1802). The lanthanide, particularly $Gd^{3+}$, chelates of N-substituted 3-hydroxy-4-pyridinones of this invention are useful as MRI contrast agents via inner-sphere mechanism. Due to their large size, the coordination numbers of lanthanide metal ions are typically 8 and 9. In solution, six coordination sites of $Gd^{3+}$ are occupied by three bidentate N-substituted 3-hydroxy-4-pyridinones while the remaining sites are available for water molecules to provide relaxation enhancement. $Fe^{3+}$ and $Mn^{2+}$ chelates of N-substituted 3-hydroxy-4-pyridinones are useful as MRI contrast agents via outer-sphere or second-sphere mechanism since they contain a dialkylamino or acylamido or sulfonylamido group, the nitrogen- or oxygen-heteroatoms of which can be used to form strong hydrogen bonds with surrounding water molecules. On the other hand, $Fe^{3+}$ and $Mn^{2+}$ chelates can be partially dissociated in biological systems to form $Fe^{3+}$ and $Mn^{2+}$ containing species, which may interact with water molecules via an inner-sphere mechanism.

The Ga-67, Tc-99m and In-111 chelates of N-substituted 3-hydroxy-4-pyridinones of this invention are useful as diagnostic radiopharmaceuticals for scintigraphic imaging. Tc-99m complexes of N-alkyl-3-hydroxypyridin-4-ones have been studied as potential radiopharmaceuticals for imaging kidney (*Nucl. Med. Biol.* 1993, 20, 857–863; *Inorg. Chem.* 1994, 33, 5607–5679) while Ga-67 complexes for imaging heart (*Nucl. Med. Biol.* 1992, 19: 327–335). In-111 complexes of N-alkyl-3-hydroxypyridin-4-ones have been used for white blood cell labeling (*J. Med. Chem.* 1996, 39: 3659–3670; *Eur. J. Nucl. Med.* 1999, 26: 1400–1406).

According to one embodiment (1) of the invention, an N-substituted 3-hydroxy-4-pyridinone compound is provided, having the following formula:

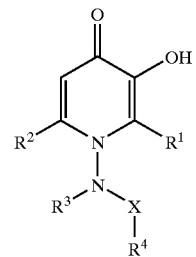

and a pharmaceutically acceptable salt thereof, wherein:

X is selected from the group: $CH_2$, C(O), C(S), $P(O)R^3R^4$, $SO_2$, C(=NH)NH, C(O)NH, and C(S)NH;

$R^1$ and $R^2$ are independently selected from: H, $C_1$–$C_{10}$ alkyl substituted with 0–5 $R^5$, $C_2$–$C_{10}$ alkenyl substituted with 0–5 $R^5$, aryl substituted with 0–3 $R^5$, and heteroaryl substituted with 0–3 $R^5$;

$R^3$ and $R^4$ are independently selected from: $C_1$–$C_{10}$ alkyl substituted with 0–5 $R^5$, $C_2$–$C_{10}$ alkenyl substituted with 0–5 $R^5$, aryl substituted with 0–3 $R^5$, heteroaryl substituted with 0–3 $R^5$, or $R^3$ and $R^4$ may be taken together to form a $C_5$–$C_7$ cyclic alkyl group optionally interrupted with O or $NR^6$;

$R^5$ is elected from: OH, $C(=O)R^6$, $C(=O)OR^6$, $C(=O)NR^6R^7$, $PO(OR^6)(OR^7)$, $S(O)_2OR^6$;

$R^6$ and $R^7$ are independently selected from: H, $C_1$–$C_{10}$ alkyl, or aryl.

Another embodiment (2) of the invention is a compound according to embodiment (1) wherein:

X is selected from the group: $CH_2$, C(O), and $SO_2$;

$R^1$ and $R^2$ are independently selected from: H, $C_1$–$C_3$ alkyl substituted with 0–2 $R^5$, and $C_2$–$C_3$ alkenyl substituted with 0–2 $R^5$;

$R^3$ and $R^4$ are independently selected from: $C_1$–$C_6$ alkyl substituted with 0–3 $R^5$, $C_2$–$C_6$ alkenyl substituted with 0–3 $R^5$, aryl substituted with 0–3 $R^5$, heteroaryl substituted with 0–3 $R^5$, or $R^3$ and $R^4$ may be taken together to form a $C_{5-7}$ cyclic alkyl group optionally interrupted with O or $NR^6$;

$R^5$ is elected from: OH, C(=O)OH, and $C(=O)NR^6R^7$;

$R^6$ and $R^7$ are independently selected from: H and $C_1$–$C_6$ alkyl.

Another embodiment (3) of the invention is a compound according to any one of embodiments (1) to (2) wherein:

X is selected from the group: $CH_2$, C(O), and $SO_2$;

$R^1$ is H;

$R^2$ is methyl or ethyl group;

$R^3$ and $R^4$ are independently selected from: aryl, heteroaryl, or $R^3$ and $R^4$ may be taken together form a 5–7 membered cyclic alkyl.

Another embodiment (4) of the invention is a compound according to any one of embodiments (1) to (2) wherein:

X is $CH_2$;

$R^1$ is H;

$R^2$ is methyl;

$R^3$ and $R^4$ are taken together form a 6-membered cyclic piperidine ring.

Another embodiment (5) of the invention is a compound according to any one of embodiments (1) to (2) wherein:

X is $CH_2$;

$R^1$ is H;

$R^2$ is methyl;

$R^3$ and $R^4$ are taken together form a 6-membered cyclic morpholine ring.

Another embodiment (6) of the invention is a compound according to any one of embodiments (1) to (2) wherein:

X is $CH_2$;

$R^1$ is H;

$R^2$ is ethyl;

$R^3$ and $R^4$ are taken together form a 6-membered cyclic morpholine ring.

Another embodiment (7) of the invention is a compound according to any one of embodiments (1) to (2) wherein:

X is C(O);

$R^1$ is H;

$R^2$ is methyl;

$R^3$ is H;

$R^4$ is phenyl.

Another embodiment (8) of the invention is a compound according to any one of embodiments (1) to (2) wherein:

X is C(O);

$R^1$ is H;

$R^2$ is ethyl;

$R^3$ is H;

$R^4$ is phenyl.

Another embodiment (9) of the invention is a compound according to any one of embodiments (1) to (2) wherein:

X is C(O);

$R^1$ is H;

$R^2$ is methyl;

$R^3$ is H;

$R^4$ is 3-pyridine.

Another embodiment (10) of the invention is a compound according to any one of embodiments (1) to (2) wherein:

X is C(O);

$R^1$ is H;

$R^2$ is methyl;

$R^3$ is H;

$R^4$ is 4-pyridine.

Another embodiment (11) of the invention is a compound according to any one of embodiments (1) to (2), wherein:

X is C(O);

$R^1$ is H;

$R^2$ is ethyl;

$R^3$ is H;

$R^4$ is 2-thiophene.

Another embodiment (12) of the invention is a compound according to any one of embodiments (1) to (2) wherein:

X is $SO_2$;

$R^1$ is H;

$R^2$ is methyl;

$R^3$ is H;

$R^4$ is phenyl.

Another embodiment (13) of the invention is a method for the preparation of an N-substituted 3-hydroxy-4-pyridinone compound according to any one of embodiments (1) to (12).

Another embodiment (14) of the invention is a pharmaceutical composition comprising a therapeutic effective amount of an N-substituted 3-hydroxy-4-pyridinone according to embodiments (1)–(12) for the treatment of iron overload.

Another embodiment (15) of the invention is a pharmaceutical composition comprising a therapeutic effective amount of an N-substituted 3-hydroxy-4-pyridinone compound according to any one of embodiments (1) to (12) and a therapeutic metal for the treatment of diseases, such as parasitic and viral infections, conditions associated with inflammation and infection, and conditions mediated by collagen formation.

Another embodiment (16) of the invention is a radiopharmaceutical of the formula:

$$M(C_h)_n,$$

and pharmaceutically acceptable salt thereof, wherein:

M is a radionuclide selected from: $^{64}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$;

n is 2 or 3;

$C_h$ is an N-substituted 3-hydroxy-4-pyridinone according to embodiments (1)–(12).

Another embodiment (17) of the invention is a radiopharmaceutical according to embodiment (16) wherein:

M is a radionuclide selected from: $^{67}Ga$, $^{68}Ga$, $^{99m}Tc$, and $^{111}In$;

n is 3;

$C_h$ is an N-substituted 3-hydroxy-4-pyridinone according to embodiments (1)–(12).

Another embodiment (18) of the invention is a radiopharmaceutical according to embodiment (16) wherein:

M is $^{111}$In;

n is 3;

$C_h$ is an N-substituted 3-hydroxy-4-pyridinone according to embodiments (1)–(12).

Another embodiment (19) of the invention is a radiopharmaceutical according to embodiment (16) wherein:

M is $^{111}$In;

n is 3;

$C_h$ is an N-substituted 3-hydroxy-4-pyridinone according to embodiment (4).

Another embodiment (20) of the invention is a radiopharmaceutical according to embodiment (16) wherein:

M is $^{111}$In;

n is 3;

$C_h$ is an N-substituted 3-hydroxy-4-pyridinone according to embodiment (5).

Another embodiment (21) of the invention is an MRI contrast agent of the formula:

$$M(C_h)_n,$$

and pharmaceutically acceptable salt thereof, wherein:

M is a paramagnetic metal ion of atomic number 21–29, 42–44, or 58–70;

n is 2 or 3;

$C_h$ is an N-substituted 3-hydroxy-4-pyridinone according to embodiments (1)–(12).

Another embodiment (22) of the invention is an MRI contrast agent according to embodiment (21) wherein:

M is selected from: $Fe^{3+}$ and $Mn^{2+}$ and $Gd^{3+}$;

n is 2 or 3;

$C_h$ is an N-substituted 3-hydroxy-4-pyridinone according to embodiments (1)–(12).

Another embodiment (23) of the invention is an MRI contrast agent according to embodiment (21) wherein:

M is $Fe^{3+}$ and $Mn^{2+}$;

n is 2 or 3;

$C_h$ is an N-substituted 3-hydroxy-4-pyridinone according to embodiments (1)–(1).

Another embodiment (24) of the invention is an MRI contrast agent according to embodiment (21) wherein:

M is $Fe^{3+}$;

n is 3;

$C_h$ is an N-substituted 3-hydroxy-4-pyridinone according to embodiments (1)–(12).

Another embodiment (25) of the invention is a method of preparing a radiopharmaceutical of any one of embodiments (16) to (20).

Another embodiment (26) of the invention is a method of preparing an MRI contrast agent of any one of embodiments (21) to (24).

Another embodiment (27) of the invention is a pharmaceutical composition comprising a metal chelate of the formula:

$$M(C_h)_n,$$

and pharmaceutically acceptable salt thereof, wherein:

M is a metal ion or a metal-containing core selected from: $Ca^{2+}$, $Sn^{2+}$, $Cu^{2+}$, $Zn^{2+}$, $V^{3+}$, $V^{5+}(O)$, or $V^{5+}(O)$—O—$V^{5+}(O)$;

n is 2 or 3;

$C_h$ is an N-substituted 3-hydroxy-4-pyridinone according to embodiments (1)–(12).

Another embodiment (28) of the invention is a method of treating of a disease such as viral infections, conditions associated with inflammation and infection, and conditions mediated by cell-proliferation or collagen formation, comprising administering a patient in need of such treatment a therapeutically effective amount of a pharmaceutical composition according to embodiment (27).

The compounds herein described may have asymmetric centers. Compounds of the invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the invention. Cis and trans geometric isomers of the compounds of the invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the invention and intermediates made therein are considered to be part of the invention.

The term "chelator" as used herein, means that any organic compound containing at least two donor atoms (e.g., oxygen, nitrogen, sulfur or phosphine). Donor atoms are used to form coordination bonds with metal ions. The chelator can be bidentate, tridentate, tetradentate, pentadentate, hexadentate, heptadentate, or octadentate depending on the number of donor atoms bonding to the metal ion.

The term "chelate" as used herein, means that any metal complex comprising a metal ion and at least one organic chelator. The metal chelate may contain one or more identical chelators, and it may also contain two (binary ligand system) or three (ternary ligand system) different chelators.

The solution stability of a metal chelate depends on the nature of metal ion, the nature of donor atoms, and the structure of the chelator or chelators. The term "stable" is meant to indicate a metal chelate that is sufficiently robust to remain in solution without significant dissociation of chelator(s).

Synthesis of metal chelates can be achieved according to the literature. For example, vanadium(V) chelates of N-substituted 3-hydroxy-4-pyridinones are prepared following the procedure disclosed in U.S. Pat. No. 6,232,340, oxovanadium(IV) chelates using the procedure disclosed in U.S. Pat. Nos. 5,866,563 and 5,527,790; and vanadium(III) chelates by the procedure disclosed in International Publication No. WO 00/24730. Zn(II), Cu(II), Sn(II) chelates N-substituted 3-hydroxy-4-pyridinones are prepared following the disclosed procedure (International Publication No. WO 00/16736; *Polyhedron* 2000, 19, 129–135; *Inorg. Chem.* 2001, 40, 4384–4388). Lanthanide chelates of N-substituted 3-hydroxypyridin-4-ones are synthesized according to the published procedure (*J. Inorg. Nucl. Chem.* 1975, 37: 1801–1802); Fe(III) chelates using the procedure disclosed in U.S. Pat. No. 6,294,152; $^{99m}$Tc chelates by procedures described in published literatures (*Nucl. Med. Biol.* 1993, 20, 857–863; *Inorg. Chem.* 1994, 33, 5607–5679); and $^{111}$In chelates using published procedures (*J. Med. Chem.* 1996, 39: 3659–3670; *Eur. J. Nucl. Med.*

1999, 26: 1400–1406). $Mn^{2+}$-containing contrast media can be manufactured according to procedures described in International Publication No. WO 96/05867, U.S. Pat. Nos. 5,525,326 and 5,716,598.

In general, a metal chelate, $M(C_h)_n$, of an N-substituted 3-hydroxypyridin-4-one is prepared by reacting the metal salt with excess chelator in the presence of a base, for example sodium hydroxide in the aqueous medium or triethylamine in a non-aqueous media like ether, methanol, ethanol, isopropanol, or acetonitrile. The $M:C_h$ ratio can be variable from 1:2 to 1:10. The preferred $M:C_h$ ratio is 1:2 for the metal chelate $M(C_h)_2$ and 1:3 for the metal chelate $M(C_h)_3$. The metal chelate is usually isolated from the reaction mixture in a solid form, and is characterized with a variety of analytical methods (HPLC, LC-MS, IR, NMR, and x-ray crystallography). The metal chelate should have sufficient chemical purity for pharmaceutical applications, and is sufficiently robust to remain in solution without significant dissociation of the chelator. For $Mn^{2+}$-based MRI contrast media, it may not be necessary to isolate the Mn-chelate from the mixture. In addition to large excess of chelator, calcium salt of the chelator is often added to reduce cardiac toxicity. The $Mn^{2+}:C_h$ ratio is up to 1:20 while the $Mn^{2+}:Ca^{2+}$ ratio is up to 1:10. In addition, the pharmaceutical composition and contrast media may contain a lyophilization aid, including but not limited to mannitol, lactose, sorbitol, dextran, Ficoll, or polyvinylpyrrolidine (PVP), a solubilization aid, such as ethanol, glycerin, polyethylene glycol, or Pluronics, and a bacteriostat, such as benzyl alcohol or benzalkonium chloride.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^5$) occurs more than one time in any constituent or formula for a compound, its definition at each occurrence is independent of its definition at every other occurrence. Thus, for example, if a group is shown to be substituted with 0–2 $R^5$, then said group may optionally be substituted with up to two $R^5$ groups. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl. "Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1, 5, 2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Therapeutically-effective amount" refers to that amount necessary to administer to a patient to achieve a therapeutic effect for the treatment of diseases, such as parasitic and viral infections, conditions associated with inflammation and infection, and conditions mediated by collagen formation. Methods of determining therapeutically-effective amounts are well known to the skilled person.

"Stable compound" and "stable structure" are meant to indicate a compound that is sufficiently robust to survive isolation to a useful degree of purity from a reaction mixture, and formulation into an efficacious therapeutic agent.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

EXAMPLES

Materials. 4-Aminomorpholine, 1-aminopiperidine, ammonium chloride, benzoylhydrazine, ethylmaltol, isonicotinic acid hydrazide, maltol, nicotinic acid hydrazide, phenylsulfonylhydrazide, sodium ascorbate, and thiophenecarboxylhydrazide were purchased from Aldrich, and were used as received. $^{111}$In Cl$_3$ (in 0.05 N HCl) were purchased from NEN®, N. Billerica, Mass.

Instruments. $^1$H NMR spectra were recorded on a 600 MHz Bruker spectrometer. The $^1$H NMR data were reported as δ (ppm) relative to TMS. LC-MS spectra were collected using a HP1100 LC/MSD system with API-electrospray interface. The ITLC method used Gelman Sciences silica gel paper strips and a mixture of acetone and saline (1:1=v:v) as eluant. By this method, the radiolabeled compound migrates to the solvent front while unchelated $^{111}$In remain at the origin.

Example I

Synthesis of N-(1-Piperidinyl)-2-Methyl-3-Hydroxy-4-Pyridinone (PMHP)

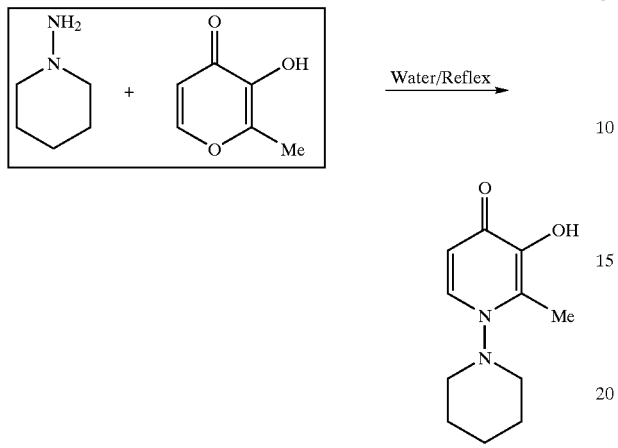

Maltol (3.6 g, 30 mmol) and 1-aminopiperidine (4.5 g, 45 mmol) were suspended in 100 mL of water. The mixture was heated to reflux for 2 days. The mixture was cooled to room temperature, and the solvent was removed under vacuum to give a dark brown liquid. The residue was allowed to stand overnight, a solid was formed. The solid was collected by filtration and was then recrystallized in water to give brownish microcrystals. The product was collected by filtration, washed with water, and dried under vacuum overnight. The yield was 0.64 g (~10.2%). LC-MS: M/z=209.3 for $[C_{11}H_{16}N_2O_2]^+$. $^1H$ NMR (600 MHz, in $CD_3OD$, chemical shift in ppm relative to TMS): 1.34 (m, 1H, $CH_2$); 1.81 (m, 5H, $CH_2$); 2.40 (s, 3H, $CH_3$); 3.00 (m, 4H, $CH_2$); 6.43 (d, 1H, $J_{HH}$=7.5 mHz, $CH_2$/pyridinone); and 7.99 (d, 1H, $J_{HH}$=7.5 mHz, CH/pyridinone).

Example II

Synthesis of N-(1-Morpholinyl)-2-Methyl-3-Hydroxy-4-Pyridinone (MMHP)

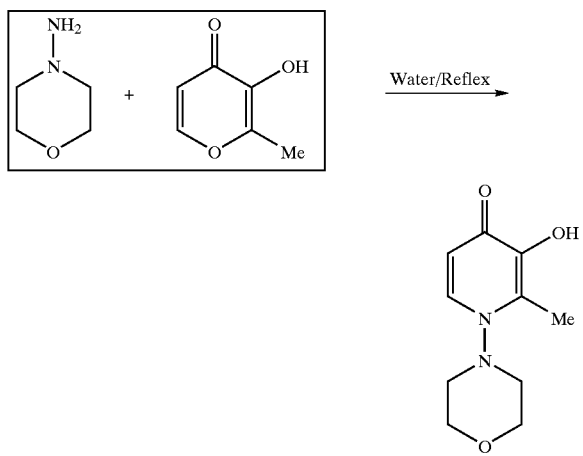

Maltol (3.6 g, 30 mmol) and 1-aminomorpholine (4.5 g, 45 mmol) were suspended in 100 mL of water. The mixture was heated to reflux for 2 days to give a dark brown solution. The solvent was removed under vacuum to give a black residue. Upon standing at room temperature overnight, a solid was formed. The solid was collected by filtration and was then recrystallized in a mixture of water/methanol (2:1=v:v) to give brownish solid. The product was collected by filtration, washed with cold methanol, and dried under vacuum overnight. The yield was 0.60 g (~9.5%). LC-MS: M/z =211.2 for $[C_{10}H_{14}N_2O_3]^+$. $^1H$ NMR (600 MHz, in $CD_3OD$, chemical shift in ppm relative to TMS): 2.50 (s, 3H, $CH_3$); 3.00 (d, 2H, $J_{HH}$=10.9 mHz, $CH_2$/morpholine); 3.29 (m, 2H, $CH_2$/morpholine); 3.79 (m, 2H, $CH_2$/morpholine); 4.00 (d, 2H, $CH_2$/morpholine); CH2/morpholine); 6.53 (d, 1H, $J_{HH}$=7.5 mHz, $CH_2$/pyridinone); and 8.09 (d, 1H, $J_{HH}$=7.5 mHz, CH/pyridinone).

Example III

Synthesis of N-(1-Morphinyl)-2-Ethyl-3-Hydroxy-4-Pyridinone (MEHP)

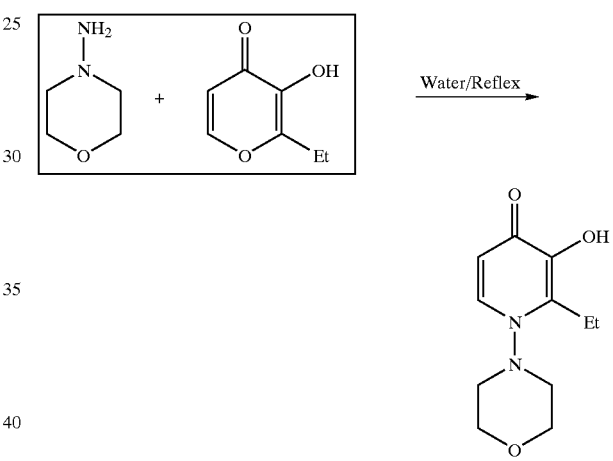

To a round-bottom flask were added ethylmaltol (3.2 g, 24 mmol), 1-aminomorpholine (4.0 g, 40 mmol) and 100 mL of water. The mixture was heated to reflux for 2 days to give a dark brown solution. Upon removal of the solvent, the dark residue was re-dissolved in a mixture of hot water/methanol (50%:50%=v:v) in the presence of charcoal. The mixture was filtered while hot. Solvents were removed under vacuum to give a black residue. After standing at room temperature for 2 days, a solid was formed. The solid was collected by filtration and was then recrystallized in a mixture of water/methanol (2:1=v:v) to give brownish microcrystals. The product was collected by filtration, washed with cold methanol, and dried under vacuum overnight. The yield was 0.48 g (~8.9%). LC-MS: M/z =225.3 for $[C_{11}H_{16}N_2O_3]^+$. $^1$ H NMR (600 MHz, in $CD_3OD$, chemical shift in ppm relative to TMS): 1.26 (t, 3H, $CH_3$); 2.95 (m, 4H, $J_{HH}$=$CH_2$/ethyl and morphine); 3.33 (m, 2H, $CH_2$/morphine); 3.80 (in, 211, $CH_2$/morphine); 4.00 (m, 2H, $CH_2$/morphine); 6.49 (d, 1H, $J_{HH}$=7.5 mHz, CH/pyridinone); and 8.05 (d, 1H, $J_{HH}$=7.5 mHz, CH/pyridinone).

Example IV

Synthesis of N-(benzoylamido)-2-Methyl-3-Hydroxy-4-Pyridinone (BMHP)

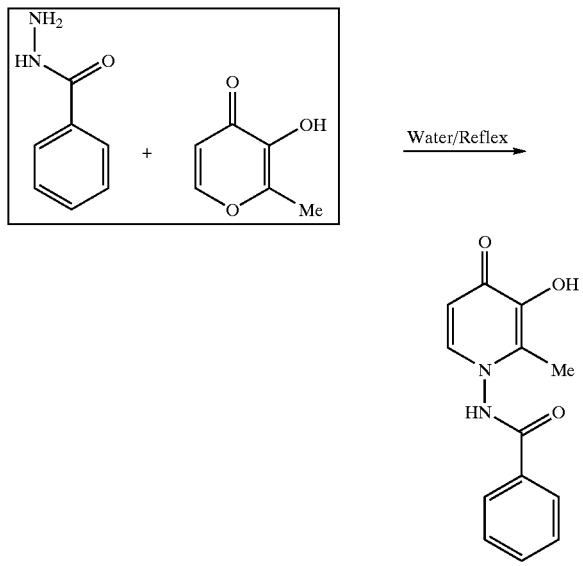

Maltol (12.5 g, 100 mmol) and benzoylhydrazine (14.5 g, 110 mmol) were suspended in 75 mL of water. The mixture was heated to reflux for 4 days, during which time a yellowish solid was formed. The mixture was filtered while hot to give 8.8 g of the product. The solid was collected and washed with hot methanol. The filtrate was evaporated under vacuum to almost dry and the residue was washed with hot methanol to give an additional 3.5 g of the product. The total yield was 12.3 g (~50%). LC-MS: M/z=245.2 for $[C_{13}H_{12}N_2O_3]^+$. $^1$H NMR (600 MHz, in $CD_3OD/CD_2Cl_2$ (2:1), chemical shift in ppm relative to TMS): 2.37 (s, 3H, $CH_3$); 6.47 (d, 1H, $J_{HH}$=7.5 mHz, CH/pyridinone); 7.55–8.00 (m, 5H, benzoyl); and 7.96 (d, 1H, $J_{HH}$=7.5 mHz, CH/pyridinone).

Example V

Synthesis of N-(isonicotinylamido)-2-Methyl-3-Hydroxy-4-Pyridinone (IMHP)

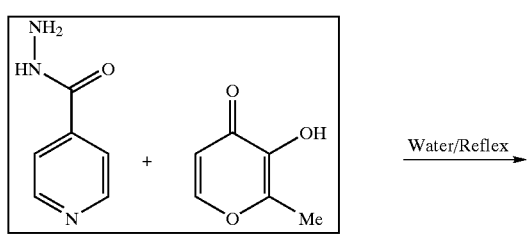

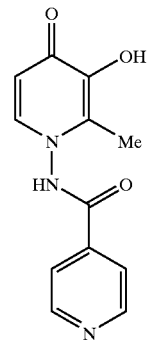

Maltol (3.6 g, 30 mmol) and isonicotinic acid hydrazide (4.35 g, 32 mmol) were suspended in 50 mL of water. The mixture was heated to reflux for 3 days. Upon cooling to room temperature, the pale-yellow solid was separated by filtration, washed with methanol. The crude product was twice recrystallized from methanol. The overall yield was 2.75 g (~37%). LC-MS: M/z=246.3 for $[C_{12}H_{11}N_3O_3]^+$. $^1$H NMR (600 MHz, in $D_2O$/NaOD, chemical shift in ppm relative to TMS): 2.30 (s, 3H, $CH_3$); 6.51 (d, 1H, $J_{HH}$=7.5 mHz, CH/pyridinone); 7.25 (d, 1H, $J_{HH}$=7.5 mHz, CH/pyridinone); 7.88 (d, 2H, $J_{HH}$=16.5 mHz, CH/pyridine); and 8.69 (d, 1H, $J_{HH}$=16.5 mHz, CH/pyridine).

Example VI

Synthesis of N-(Nicotinylamido)-2-Methyl-3-Hydroxy-4-Pyridinone (NMHP)

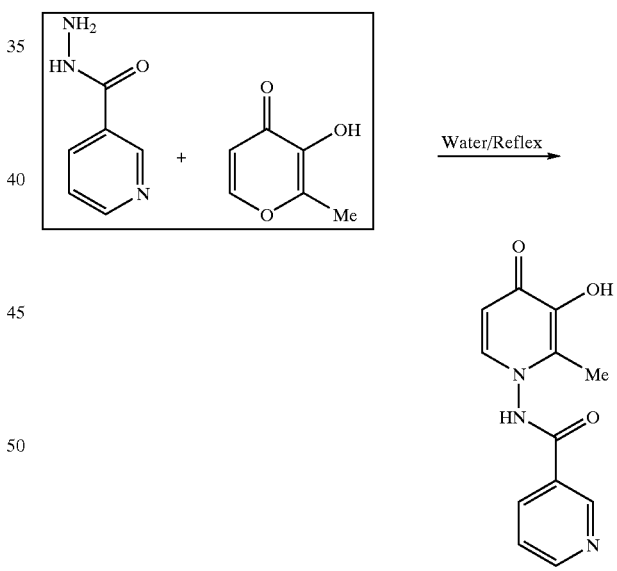

Maltol (12.1 g, 100 mmol) and nicotinic acid hydrazide (14.2 g, 100 mmol) were suspended in 50 mL of water. The mixture was heated to reflux for 3 days. Upon cooling to room temperature, the pale-yellow solid was formed. The solid was separated by filtration, washed with methanol. The crude product was recrystallized twice from methanol. The purified product was dried under vacuum. The yield was 15.0 g (~61%). LC-MS: M/z=246.3 for $[C_{12}H_{11}N_3O_3]^+$. $^1$H NMR (600 MHz, in $D_2O$/NaOD, chemical shift in ppm relative to TMS): 2.32 (s, 3H, $CH_3$); 6.52 (d, 1H, $J_{HH}$=7.5 mHz, CH/pyridinone); 7.28 (d, 1H, CH/pyridinone); 7.62

(m, 1H, CH/pyridine); 8.35 (m, 1H, CH/pyridine); 8.70 (d, 1H, $J_{HH}$=5.0 mHz, CH/pyridine); and 8.69 (s, 1H, CH/pyridine).

Example VII

Synthesis of N-(Thiophenecarboxylamido)-2-Methyl-3-Hydroxy-4-Pyridinone (TMHP)

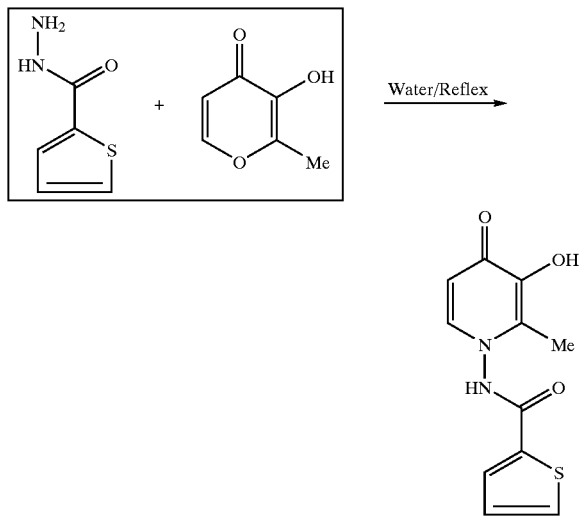

Maltol (3.6 g, 30 mmol) and thiophenecarboxylhydrazide (4.26 g, 30 mmol) were suspended in 50 mL of water. The mixture was heated to reflux for 7 days, during which time a pale-yellow solid was formed. The solid was separated by filtration, washed with hot methanol. The crude product was recrystallized twice from methanol. The purified product was dried under vacuum overnight. The yield was 1.95 g (~26%). LC-MS: M/z=251.3 for $[C_{11}H_{10}N_2O_3S]^+$. $^1$H NMR (600 MHz, in D$_2$O/NaOD, chemical shift in ppm relative to TMS): 2.28 (s, 3H, CH$_3$); 6.48 (m, 1H, $J_{HH}$=7.5 mHz, CH/pyridinone); 7.26 (m, 2H, CH/pyridinone and thiophene); 7.64 (d, 1H, $J_{HH}$=5.0 mHz, CH/thiophene); and 7.71 (d, 1H, $J_{HH}$=3.7 mHz, CH/thiophene).

Example VIII

Synthesis of N-(Phenylsulfonylamido)-2-Methyl-3-Hydroxy-4-Pyridinone (PSMHP)

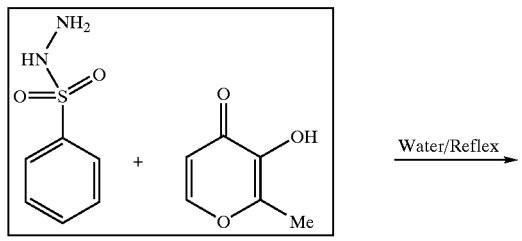

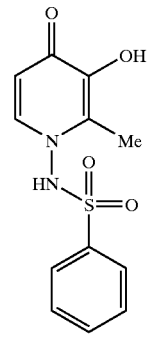

Maltol (12.1 g, 100 mmol) and phenylsulfonylhydrazine (17.2 g, 100 mmol) were suspended in 100 mL of water. The mixture was heated to reflux for 2 days. After cooling to room temperature the semi-solid residue was separated, and washed with hot methanol. The white solid was separated by filtration. The crude product was recrystallized from methanol. The purified product was dried under vacuum overnight. The yield was 2.15 g (~7.7%). LC-MS: M/z=281.2 for $[C_{12}H_{12}N_2O_4S]^+$. $^1$H NMR (600 MHz, in D$_2$O/NaOD, chemical shift in ppm relative to TMS): 2.11 (s, 3H, CH$_3$); 6.26 (d, 1H, $J_{HH}$=7.1 mHz, CH/pyridinone); 7.08 (d, 1H, $J_{HH}$=7.1 mHz, CH/pyridinone); and 7.60–7.90 (m, 5H, phenyl).

Example IX

Synthesis of $^{111}$In(PMHP)$_3$

To a clean 5 mL vial were added 5 mg of PMHP, 1.5 mL of 0.5 M NH$_4$OAc (pH=6.0), 0.5 mL of ethanol, and 4 µL of $^{111}$InCl$_3$ solution (~0.5 mCi) in 0.05 N HCl. The reaction mixture was allowed to stand at room temperature for ~20 min. The resulting solution was analyzed by an ITLC method using Gelman Sciences silicon gel paper strip, and a 50:50 mixture of saline and acetone as mobile phase. Using this method, $^{111}$InCl$_3$ and [$^{111}$In]acetate remain at the origin while the radiolabeled $^{111}$In(PMHP)$_3$ migrates to the solvent front. The yield was 98%.

Example X

Synthesis of $^{111}$In(MMHP)$_3$

To a clean 5 mL vial were added 5 mg of MMHP, 1.5 mL of 0.5 M NH$_4$OAc (pH=6.0), 0.5 mL of ethanol, and 4 µL of $^{111}$InCl$_3$ solution (~0.5 mCi) in 0.05 N HCl. The reaction mixture was allowed to stand at room temperature for ~20 min. The resulting solution was analyzed by an ITLC method using Gelman Sciences silicon gel paper strip, and a 50:50 mixture of saline and acetone as mobile phase. Using this method, $^{111}$InCl$_3$ and [$^{111}$In]acetate remain at the origin while the radiolabeled $^{111}$In(MMHP)$_3$ migrates to the solvent front. The yield was 99%.

Utility

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the invention may be used in a similar manner as other MRI agents as described in U.S. Pat. Nos. 5,155,215; 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

Oncomouse® Imaging

The study involves the use of the c-Neu Oncomouse® and FVB mice simultaneously as controls. The mice are anesthetized with sodium pentobarbital and injected with approximately 0.5 mCi of radiopharmaceutical. Prior to injection, the tumor locations on each Oncomouse® are recorded and tumor size measured using calipers. The animals are positioned on the camera head so as to image the anterior or posterior of the animals. 5 Minute dynamic images are acquired serially over 2 hours using a 256×256 matrix and a zoom of 2×. Upon completion of the study, the images are evaluated by circumscribing the tumor as the target region of interest (ROI) and a background site in the neck area below the carotid salivary glands.

This model can be used to assess the effectiveness of the radiopharmaceuticals of the invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of radiopharmaceuticals can be assessed by monitoring the rate of growth of the tumors in control mice versus those in the mice administered the radiopharmaceuticals of the invention.

Rabbit Matrigel Model

This model was adapted from a matrigel model intended for the study of angiogenesis in mice. Matrigel (Becton & Dickinson, USA) is a basement membrane rich in laminin, collagen IV, entactin, HSPG and other growth factors. When combined with growth factors such as bFGF [500 ng/ml] or VEGF [2 µg/ml] and injected subcutaneously into the mid-abdominal region of the mice, it solidifies into a gel and stimulates angiogenesis at the site of injection within 4–8 days. In the rabbit model, New Zealand White rabbits (2.5–3.0 kg) are injected with 2.0 ml of matrigel, plus 1 µg bFGF and 4 µg VEGF. The radiopharmaceutical is then injected 7 days later and the images obtained.

This model can also be used to assess the effectiveness of radiopharmaceuticals of the invention comprised of a beta, alpha or Auger electron emitting isotope. The radiopharmaceuticals are administered in appropriate amounts and the uptake at the angiogenic sites can be quantified either non-invasively by imaging for those isotopes with a coincident imageable gamma emission, or by excision of the angiogenic sites and counting the amount of radioactivity present by standard techniques. The therapeutic effect of radiopharmaceuticals can be assessed by monitoring the rate of growth of the angiogenic sites in control rabbits versus those in the rabbits administered the radiopharmaceuticals of the invention.

Imaging of the laterals were for 2 hours with a 256×256 matrix, no zoom, 5 minute dynamic images. A known source is placed in the image field (20–90 µCi) to evaluate region of interest (ROI) uptake. Images were also acquired 24 hours post injection to determine retention of the compound in the tumor. The uptake is determined by taking the fraction of the total counts in an inscribed area for ROI/source and multiplying the known µCi. The result is µCi for the ROI.

This model can also be used to assess the effectiveness of the radiopharmaceuticals of the invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the size of the tumors over time.

Obviously, numerous modifications and variations of the invention are possible in light of the above teachings. It is therefore to be understood that within the scope of the appended claims, the invention may be practiced otherwise that as specifically described herein.

What is claimed is:

1. A radiopharmaceutical of the formula:

$$M(C_h)_n,$$

or pharmaceutically acceptable salt thereof, wherein:

M is a radionuclide selected from: $^{64}$Cu, $^{67}$Cu, $^{67}$Ga, $^{68}$Ga, $^{99m}$Tc, $^{111}$In, $^{90}$Y, $^{149}$Pr, $^{153}$Sm, $^{159}$Gd, $^{166}$Ho, $^{169}$Yb, $^{177}$Lu, $^{86}$Re, and $^{188}$Re;

$C_h$ is an N-substituted 3-hydroxy-4-pyridinone compound of the formula (I):

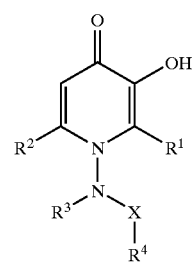

(I)

or a pharmaceutically acceptable salt thereof, wherein:

X is selected from the group: $CH_2$, C(O), C(S), P(O)R$^3$R$^4$, SO$_2$, C(=NH)NH, C(O)NH, and C(S)NH;

R$^1$ and R$^2$ are independently selected from: H, $C_1$–$C_{10}$ alkyl substituted with 0–5 R$^5$, $C_2$–$C_{10}$ alkenyl substituted with 0–5 R$^5$, aryl substituted with 0–3 R$^5$, and heteroaryl substituted with 0–3 R$^5$;

R$^3$ and R$^4$ are independently selected from: $C_1$–$C_{10}$ alkyl substituted with 0–5 R$^5$, $C_2$–$C_{10}$ alkenyl substituted with 0–5 R$^5$, aryl substituted with 0–3 R$^5$, and heteroaryl substituted with 0–3 R$^5$, or R$^3$ and R$^4$ may be taken together to form a $C_5$–$C_7$ cyclic alkyl group optionally interrupted with O or NR$^6$;

R$^5$ is selected from: OH, C(=O)R$^6$, C(=O)OR$^6$, C(=O)NR$^6$R$^7$, PO(OR$^6$)(OR$^7$), and S(O)$_2$OR$^6$;

R$^6$ and R$^7$ are independently selected from: H, $C_1$–$C_{10}$ alkyl, and aryl; and n is 2 or 3.

2. The radiopharmaceutical according to claim 1 wherein:

M is a radionuclide selected from: $^{67}$Ga, $^{68}$Ga, $^{99m}$Tc, and $^{111}$In; and n is 3.

3. The radiopharmaceutical according to claim 1 wherein:

M is $^{111}$In; and n is 3.

4. The radiopharmaceutical according to claim 1 wherein:

M is $^{111}$In;

n is 3.

X is $CH_2$;

$R^1$ is H;

$R^2$ is methyl; and $R^3$ and $R^4$ are taken together form a 6-membered cyclic piperidine ring.

5. The radiopharmaceutical according to claim 1 wherein:

M is $^{111}$In;

n is 3;

X is $CH_2$;

$R^1$ is H;

$R^2$ is methyl; and $R^3$ and $R^4$ are taken together form a 6-membered cyclic morpholine ring.

6. A method of preparing a radiopharmaceutical of claim 1, comprising the step of:

reacting a salt of said radionuclide with an excess of said N-substituted 3-hydroxy-4-pyridinone compound of the formula (I).

* * * * *